United States Patent [19]

Cockman et al.

[11] Patent Number: 6,072,090
[45] Date of Patent: Jun. 6, 2000

[54] OLEFIN HYDRATION PROCESS

[75] Inventors: Russell William Cockman, Stirlingshire; Mark Royston Smith, Clackmannanshire, both of United Kingdom

[73] Assignee: BP Chemicals Limited, London, United Kingdom

[21] Appl. No.: 09/263,085

[22] Filed: Mar. 8, 1999

[30] Foreign Application Priority Data

Mar. 25, 1998 [GB] United Kingdom ................. 9806408

[51] Int. Cl.$^7$ .................................................. C07C 29/04
[52] U.S. Cl. ........................ 568/896; 568/898; 568/901
[58] Field of Search .................... 568/896, 901, 568/898

[56] References Cited

U.S. PATENT DOCUMENTS

| | | | |
|---|---|---|---|
| 2,162,913 | 6/1939 | Eversole | 568/896 |
| 2,173,187 | 9/1939 | Tanner | 568/896 |
| 2,232,610 | 2/1941 | Joshua et al. | |
| 3,758,615 | 9/1973 | Izumi | 568/896 |
| 3,996,298 | 12/1976 | Izumi | 568/896 |
| 4,351,971 | 9/1982 | Kanemaru et al. | |
| 5,488,185 | 1/1996 | Ramachandran | 5268/896 |
| 5,616,815 | 4/1997 | Atkins | 568/700 |
| 5,629,459 | 5/1997 | Atkins | 568/896 |
| 5,684,216 | 11/1997 | Haining | 568/896 |
| 5,714,429 | 2/1998 | Haining | 502/232 |

FOREIGN PATENT DOCUMENTS

| | | |
|---|---|---|
| 0 704 240 A1 | 4/1996 | European Pat. Off. . |
| 0 713 723 A1 | 5/1996 | European Pat. Off. . |
| 0 713 847 A2 | 5/1996 | European Pat. Off. . |

*Primary Examiner*—Michael L. Shippen
*Attorney, Agent, or Firm*—Nixon & Vanderhye

[57] ABSTRACT

This invention relats to a continuous process for the hydration of olefins with water in the vapour phase to the corresponding alcohol in the presence of a heteropolyacid salt as catalyst said process including the recycle of un-reacted olefin back to the hydration reaction characterised in that the heteropolyacid salt is a metal salt of silicotungstic acid or phosphotungstic acid which is soluble in a polar solvent below 40° C. wherein the metal in the salt is an alkali metal or an alkaline earth metal.

9 Claims, No Drawings

OLEFIN HYDRATION PROCESS

The present invention relates to a process for the hydration of olefins to alcohols using a heteropolyacid salt as catalyst.

Hydration of olefins such as ethylene or propylene to the corresponding alcohols by hydration thereof in the vapour phase using a phosphoric acid catalyst deposited on a siliceous support is well known. Numerous prior art publications described such a procedure including those disclosed in GB-A-1570650, U.S. Pat. No. 4,808,559, GB-A-1371905, U.S. Pat. No. 4,038,211, U.S. Pat. No. 4,012,452, GB-A-1476534, GB-A-1306141, U.S. Pat. No. 3,996,338 and CAN-A-844004. In each of these prior publications, the nature of the siliceous support used is defined by various parameters including the pore volume, the surface area, the crush strength and the purity of the support.

Some of the prior art publications such as eg GB-A-1281120 describe a liquid phase process for the hydration of olefins using a heteropolyacid catalyst. Furthermore, U.S. Pat. No. 2,173,187 describes a process for the hydration of olefins in the vapour phase to the corresponding alcohols by using as catalyst a heteropolyacid, the complex anion of which includes one element from Group VI, sub-Group A of the Periodic table. It is stated in this reference that the catalyst can be used with or without a support. The supports, when used, are said to be preferably silica gel although other siliceous supports such as silicic acid, Japanese acid clay, bentonite, kieselguhr, or asbestos are also listed. Similarly, JA-A-57130935 describes a process for olefin hydration using a heteropolyacid catalyst supported on activated carbon. Furthermore, U.S. Pat. No. 2,608,534 describes a heteropolyacid supported on a major amount of an inorganic metal oxide or hydroxide as catalyst for a number of general organic reactions including inter alia the hydration of olefins. Amongst the supports disclosed in this publication are alumina, magnesia, thoria, titania and the like and alumina is said to be preferred.

One of the problems of using free heteropolyacids as catalysts for the hydration of olefins such as ethylene and propylene to the corresponding alcohols is that these catalysts are highly reactive and the reactions tend to be highly exothermic thereby making the start-up and running such a plant hazardous on a commercial scale. Moreover, the use of free heteropolyacid catalysts show good performance when used in a single pass reaction. However, the conversion of ethylene per pass is normally only around 6%. Therefore, in a commercial operation, it is necessary to recycle the un-reacted ethylene back to the reactor. If, however, the free heteropolyacid catalyst is used in a continuous process which involves the recycle of the un-reacted olefin back to the hydration reactor in order to maximise the utilisation of the olefinic feedstock, the presence of trace impurities such as eg aldehydes, ethers, some alcohols and some dimers/polymers of the olefin in such recycled olefin tends to substantially deactivate or disintegrate the catalyst. Furthermore, whilst some salts of heteropolyacids have been recommended for use in some prior publications for the olefin hydration reaction none of the salts used can be termed as being readily soluble under ambient conditions in readily available solvents, in most instances due to the high concentration of cations present in the salt eg from 6–12 moles of potassium per mole of heteropolyacid which adversely affect the solubility thereof Moreover, none of these salts have been used in a continuous process for olefin hydration which involve the recycle of the un-reacted olefin back to the hydration reactor. Thus, there has been no disclosure hitherto of any specific heteropolyacid salt as a catalyst in a continuous specific process for the hydration of olefins to the corresponding alcohols which mitigates the above problems.

It has now been found that the process can be improved by using specific salts of heteropolyacids as catalyst which have controlled activity and further improved by using specific process conditions.

Accordingly, the present invention is a continuous process for the hydration of olefins with water in the vapour phase to the corresponding alcohol in the presence of a heteropolyacid salt as catalyst said process including the recycle of un-reacted olefin back to the hydration reaction characterised in that the heteropolyacid salt is a salt of silicotungstic acid or phosphotungstic acid which is soluble in a polar solvent below 40° C. wherein the metal in the salt is an alkali metal or an alkaline earth metal.

The term "heteropolyacids" as used herein and throughout the specification is meant to represent silicotungstic acid and phosphotungstic acid with or without any water of crystallisation.

By "polar solvent" is meant here and throughout the specification one or more of water and lower aliphatic alcohols (e.g. C1–C4 alcohols) or glycols (C2–C5 glycols) and ketones (eg acetone or methyl ethyl ketone).

The catalyst suitably has no more than four moles of alkali metal cation, or two moles of alkaline earth metal cation, per mole of heteropolyacid, preferably there are one to two mono-valent cations in the heteropolyacid salt. Thus, it is preferably the mono- or the di-potassium salt. The catalyst is suitably supported on a siliceous support and the supported catalyst will hereafter be termed "catalyst system". Specific examples of such supports include, silica gel or synthetic silicas prepared eg from fumed silicas or flame hydrolysis of silicon tetrachloride. The support may be in any suitable physical form such as eg granules, pellets or extrudates. Such grades of silicas are available as proprietary products from Grace (Grade 57) and Degussa (Degussa 350) respectively. The supported catalyst (catalyst system) is suitably prepared by impregnating the support with a solution of a salt of the heteropolyacid which is prepared in turn by dissolving the heteropolyacid salt in a solvent such as eg an alcohol or distilled water. The support is then added to the solution so formed. The support is suitably left to soak in the solution of the heteropolyacid salt for a duration of several hours, with periodic manual stirring, after which time it is suitably filtered using a Buchner funnel in order to remove any excess acid salt. Other impregnation techniques such as the incipient wetness technique can also be used.

The wet catalyst thus formed is then suitably placed in an oven at elevated temperature for several hours to dry, after which time it is allowed to cool to ambient temperature in a desiccator. The weight of the catalyst on drying, the weight of the support used and the weight of the acid on support was obtained by deducting the latter from the former from which the catalyst loading in g/liter was determined. This catalyst system (measured by weight) was then used in the olefin hydration process.

The degree of hydration of the heteropolyacid may affect the acidity of the catalyst and hence its activity. Thus, either or both of these actions of impregnation and olefin hydration process may possibly change the hydration and oxidation state of the metals in the salts of the heteropolyacids, ie the actual catalytic species under the process conditions may not retain the hydration/oxidation states of the metals in the salts of the heteropolyacids used to impregnate the support. Naturally, therefore, it is to be expected that such hydration and oxidation states may also be different in the spent catalysts after the reaction.

The supported heteropolyacid salt catalyst (catalyst system) may also be further modified by the addition of phosphoric acid or other mineral acids thereto.

The process is suitably carried out using the following reaction conditions:

a. the mole ratio of water to olefin passing through the reactor is suitably in the range from 0.1–3.0, preferably 0.1–1.0 b. the gas hourly space velocity (GHSV) of the water/olefin mixture is suitably from 0.010 to 0.25 g/min/cm$^3$ of the catalyst system, preferably from 0.03–0.10 g/min/cm$^3$ of the catalyst system.

c. the heteropolyacid catalyst concentration is from 5 to 40% w/w based on the total weight of the catalyst system, preferably from 10–30% w/w of the total weight of the catalyst system.

The olefin hydration reaction is carried out at a temperature from 150–350° C. Within this temperature range, the hydration of ethylene to ethanol is suitably carried out at a temperature in the range from its dew point to 350° C., and preferably from 200–300° C.; the hydration of propylene to isopropanol is suitably carried out at a temperature in the range from its dew point to 300° C., and is preferably from 150–250° C.

The olefins to be hydrated are suitably ethylene or propylene and the corresponding alcohols formed are suitably ethanol and isopropanol respectively. These olefins may be used pure or as a mixture of olefins to generate a corresponding mixture of alcohols. Thus mixed hydrocarbon feedstocks emerging from eg a refinery such as from a fluid catalytic cracking process and comprising a mixture of C2 and C3 saturated and unsaturated hydrocarbons can be used for this purpose. The process is carried out in the vapour phase, ie both the olefin and water are in the vapour phase over the catalyst system, apart from a small proportion of each gaseous reactant which dissolves in the catalyst system. The hydration reaction is believed to occur between such dissolved reactants. Ethers corresponding to the olefin are formed as by-products during the reaction. The process is further improved and optimised by recycling the un-reacted olefin, if desired after removal of undesirable impurities therefrom, back to the reactor.

The hydration reaction is carried out by placing the catalyst system in a reactor, sealing the reactor and then heating the catalyst system to the reaction temperature. The catalyst system is heated to a temperature from 150 to 300° C. depending upon the end product desired. For instance, if the end product is ethanol from ethylene, the catalyst system is suitably heated from 200 to 280° C., preferably from 200–260° C., more preferably from 210–245° C. On the other hand, if the end product is isopropanol from propylene, the catalyst system is suitably heated to a temperature in the range, slightly above the dew point to 225° C., or preferably, a temperature in the range, from slightly above the dew point to 185° C. When the catalyst system has attained the desired temperature a charge of the olefin and water in the vapour state is passed through the reactor. The mole ratio of water to olefin passing through the reactor is suitably in the range from 0.1 to 3.0, preferably from 0.1 to 1.0, more preferably from 0.25–0.45. The space velocity of water vapour/olefin mixture passing through the reactor is subject to slight variations depending upon whether the reactant olefin is ethylene or propylene. For instance, in the case of ethylene, the space velocity of the mixture thereof with water vapour is suitably from 0.010 to 0.100, preferably from 0.020 to 0.050 grams per minute per cm$^3$ of the catalyst system. In the case of a mixture of propylene and water vapour, the space velocity is suitably in the from 0.010–0.100, preferably from 0.02–0.07 g/min/cm$^3$ of the catalyst system.

The hydration reaction is carried out at a pressure ranging from 1000–25000 KPa. Within this range, the hydration of ethylene is suitably carried out at a pressure from 3000 to 10000 KPa, whereas the hydration of propylene is suitably carried out at a pressure from 2000–7600 KPa.

The activity of the catalyst system was measured by monitoring the total amount of alcohol, ether and un-reacted olefin produced over a one-hour period at standard test conditions (specified in the Examples below).

Alcohol and ether production was measured by gas chromatography (see below), whereas un-reacted olefin was metered using a wet-type positive displacement flow meter.

Thus, it has now been found that by using the specific catalyst system described herein it is possible not only to increase the space-time-yield (hereafter "STY") and selectivity of the process but also to prolong the life of the catalyst/support thereby reducing the frequency with which the catalyst/support is changed or replaced on a plant.

The present invention is further illustrated with reference to the following examples:

EXAMPLE 1

Catalyst Preparation 12-tungstosilicic acid.xH$_2$O (x$\simeq$24, 370 g) was dissolved in distilled water (800 ml) to which was added orthophosphoric acid (1.488 g of 85%w/w strength). In a separate container KHCO$_3$ (11.15 g) was dissolved in water (50 ml) and then slowly added, with stirring, to the acid solution. The container was rinsed three times with distilled water (50 ml, total volume added 150 mi) and the washings were added to the acid solution. (The quantity of KHCO$_3$ was chosen so as to provide one molar equivalent of potassium per mole of 12-tungstosilicic acid.xH$_2$O dissolved in the solution). The solution was stirred for 15 minutes after the evolution of CO$_2$ had ceased. Then Grace57 silica (1.21), an essentially pure silica carrier (>99.8%w/w silica), was added and allowed to soak for 24 hours. After soaking, the catalyst was drained of excess solution for 1 hour and then dried in air for 16 hours at 105° C. One liter of finished catalyst weighed 551 g, giving an acid loading of 151 g/l.

Operation

In a plant utilising recycled (un-reacted) ethylene the gaseous product exiting the reactor was cooled to 20° C. in a high pressure cooler before passing to a high pressure gas-liquid separator for separating the water-rich and ethylene-rich phases. The water-rich phase, which contained a major proportion of the product ethanol and also by-product diethylether and acetaldehyde, was passed through a control valve to a collection pot at ambient pressure. The ethylene-rich stream from the gas-liquid separator was then passed to the bottom of the water wash tower where it met a countercurrent stream of water which stripped the majority of the remaining ethanol from the gaseous stream flowing upwards. The purified gaseous stream, which was predominantly ethylene, but contained in the region of 90 mg/l of diethylether, 5 mg/l of acetaldehyde and less than 0.5 mg of ethanol per liter of gas (as measured at normal temperatures and pressures), was then passed to the recycle machine for feeding back to the reactor. The flow of water into the wash tower was in the region of 1300 ml/hr and the level in the tower was maintained by a level control system and liquid off-take control valve. The liquid exiting the wash tower is mixed with the liquid product from the gas-liquid separator and contained the ethanol product of the plant.

Conditions

One liter of catalyst (acid loading 151 g/l), as prepared in Example 1 above, was loaded into the reactor. After the plant was started-up ethylene was introduced and conditions were adjusted to target and stabilised. Reactor inlet pressure was 6980 KPa; reactor inlet temperature was 225.1° C.; reactor exit temperature was 245.6° C.; ethylene recycle flow rate was 1500 g/hr; reactor inlet water:ethylene mole ratio was 0.387; wash tower water flow rate was 1300 ml/hr running at the ambient temperature of 21° C. (pref. 20–30° C.).

The following performance was achieved in the pilot plant by the catalyst of Example 1; ethanol productivity, 163.5 STY; diethylether, 7.02 STY; acetaldehyde, 0.60 STY; selectivity to ethanol, 94.6% (selectivity is defined as: the ratio of the moles of ethylene converted to ethanol to the total moles of ethylene converted to products).

Comparative Test not according to the invention

An experiment, carried out in similar fashion to that of Example 1, but in a plant where the un-reacted ethylene was not recycled back to the reactor is now described. The data have been produced in a plant operating a reactor containing 50 ml of catalyst similar to that of Example 1 under isothermal conditions scaled by a factor of 20 for comparison with the catalyst scale of Example 1.

Reactor inlet pressure was 4825 KPa; reactor inlet temperature was 235.0° C.; ethylene flow rate was 1440 g/hr and reactor inlet water:ethylene mole ratio was 0.30.

The following performance was achieved in the pilot plant by the catalyst of this comparative test; ethanol productivity, 97 STY; diethylether, 163 STY; acetaldehyde, 7.2STY; selectivity to ethanol, 31.6% (selectivity defined as above).

We claim:

1. A continuous process for the hydration of olefins with water in the vapor phase to the corresponding alcohol in the presence of a heteropolyacid salt as catalyst, said process comprising recycling of un-reacted olefin back to the hydration reaction, wherein the heteropolyacid salt is a mono- or di-potassium salt of silicotungstic acid or phosphotungstic acid which is soluble in a polar solvent below 40° C.

2. A process as claimed in claim 1, wherein the catalyst has no more than four moles of alkali metal cation, or two moles of alkaline earth metal cation, per mole of heteropolyacid.

3. A process as claimed in claim 1, wherein the catalyst is supported on a siliceous support.

4. A process as claimed in claim 1, wherein the olefin hydration reaction is carried out by passing the olefin to be hydrated and water over the catalyst in a mole ratio of 0.1–3.0, and at a gas hourly space velocity (GHSV) of 0.010 to 0.25 g/min/cm$^3$.

5. A process as claimed in claim 3 wherein the catalyst concentration is from 5 to 60% w/w based on the total weight of the supported catalyst.

6. A process as claimed in claim 1, wherein the olefin hydration reaction is carried out at a temperature from 150–350° C.

7. A process as claimed in claim 1, wherein the olefin comprises ethylene, propylene or a mixture thereof.

8. A process as claimed in claim 7, wherein the olefin comprises ethylene and the hydration reaction is carried out at a temperature of 200–300° C.

9. A process as claimed in claim 7, wherein the olefin comprises propylene and the hydration reaction is carried out at a temperature of 150–250° C.

* * * * *